(12) United States Patent
Villax et al.

(10) Patent No.: US 8,677,992 B2
(45) Date of Patent: Mar. 25, 2014

(54) SIMPLE CAPSULE-BASED INHALER

(75) Inventors: Peter Villax, Lisbon (PT); Pedro J. Mendes, Lisbon (PT); Iain G. Mcderment, Melbourn (GB)

(73) Assignee: Hovione International Ltd., Wanchai (HK)

( * ) Notice: Subject to any disclaimer, the term of this patent is extended or adjusted under 35 U.S.C. 154(b) by 378 days.

(21) Appl. No.: 13/094,108

(22) Filed: Apr. 26, 2011

(65) Prior Publication Data

US 2011/0259328 A1    Oct. 27, 2011

(30) Foreign Application Priority Data

Apr. 26, 2010    (PT) .......................................... 105065

(51) Int. Cl.
    *A61M 15/00*    (2006.01)
(52) U.S. Cl.
    USPC ............ 128/203.21; 128/203.12; 128/203.15; 128/203.23
(58) Field of Classification Search
    USPC ......................... 128/200.24, 203.12, 203.15, 128/203.18–203.19, 203.21–203.24, 128/203.28; 604/57, 58; 222/5, 80–91, 222/541.2; 606/184; 225/37, 40; 30/2
    See application file for complete search history.

(56) References Cited

U.S. PATENT DOCUMENTS

| | | | |
|---|---|---|---|
| 3,518,992 A | 7/1970 | Altounyan et al. | |
| 4,889,114 A | 12/1989 | Kladders | |
| 5,645,050 A * | 7/1997 | Zierenberg et al. | 128/203.15 |
| 5,673,686 A | 10/1997 | Villax et al. | |
| 6,298,846 B1 * | 10/2001 | Ohki et al. | 128/203.15 |
| 6,422,236 B1 * | 7/2002 | Nilsson et al. | 128/203.15 |
| 6,470,884 B2 | 10/2002 | Horlin | |
| 6,478,806 B2 * | 11/2002 | McFarlane | 606/185 |
| 6,591,833 B2 * | 7/2003 | Datta et al. | 128/203.15 |
| 6,766,799 B2 * | 7/2004 | Edwards et al. | 128/203.15 |
| 6,772,755 B2 | 8/2004 | Pera | |
| 7,451,761 B2 * | 11/2008 | Hickey et al. | 128/203.21 |
| 7,832,399 B2 * | 11/2010 | Ganem et al. | 128/203.21 |
| 2002/0121277 A1 | 9/2002 | Pera | |
| 2003/0131847 A1 | 7/2003 | Niccolai | |
| 2006/0254583 A1 | 11/2006 | Deboeck et al. | |
| 2007/0283955 A1 | 12/2007 | Tsutsui | |
| 2009/0090362 A1 * | 4/2009 | Harmer et al. | 128/203.21 |
| 2009/0178676 A1 * | 7/2009 | Villax et al. | 128/203.15 |
| 2009/0194105 A1 | 8/2009 | Besseler et al. | |
| 2009/0320838 A1 | 12/2009 | Malhotra et al. | |
| 2010/0275917 A1 | 11/2010 | Kuhn et al. | |
| 2010/0300440 A1 | 12/2010 | Deboeck et al. | |

FOREIGN PATENT DOCUMENTS

| | | |
|---|---|---|
| EP | 1245243 A1 | 10/2002 |
| FR | 21844 E | 3/1921 |

(Continued)

*Primary Examiner* — Justine Yu
*Assistant Examiner* — Timothy Stanis
(74) *Attorney, Agent, or Firm* — Dickstein Shapiro LLP

(57) ABSTRACT

A dry powder inhaler for pulmonary or nasal use, employing capsules containing a dose of powder for inhalation, comprising two operating components and an optional cover. Air is drawn by the patient via a mouthpiece or nosepiece which is in communication with the capsule and travels via air paths through the device and through the capsule thereby dispersing and entraining the dose of powder. The capsule is cut by cutting means located on one of the components, in a manner which eliminates or minimizes capsule debris and minimizes powder leakage during use. The inhaler body and capsule cutting blades comprise a single operating component and they may be manufactured in a single unitary step. The invention affords a very economical and simple device for the delivery of pulmonary medicines.

20 Claims, 6 Drawing Sheets

(56) References Cited

FOREIGN PATENT DOCUMENTS

| | | |
|---|---|---|
| GB | 1182779 A | 3/1970 |
| PT | 101450 A | 8/1995 |
| WO | WO-2004082750 A1 | 9/2004 |
| WO | WO-2007093149 A1 | 8/2007 |
| WO | WO-2007098870 A1 | 9/2007 |
| WO | WO-2007144659 A1 | 12/2007 |
| WO | WO-2009013218 A1 | 1/2009 |
| WO | WO-2009117112 A2 | 9/2009 |
| WO | WO-2009139732 A1 | 11/2009 |

* cited by examiner

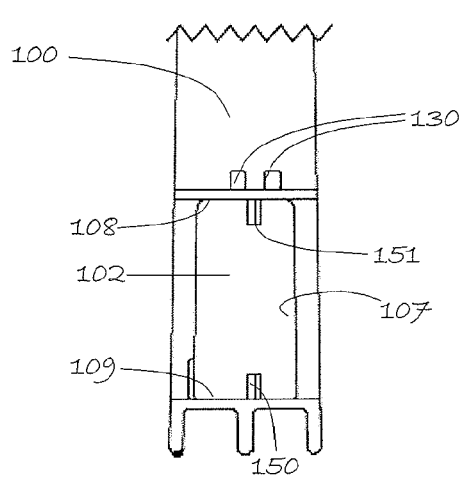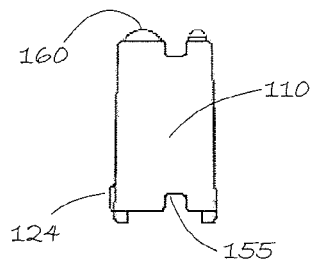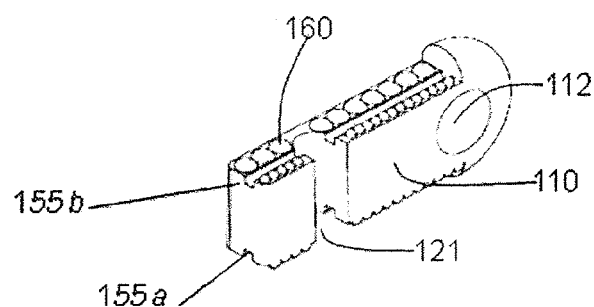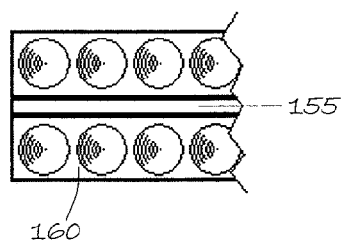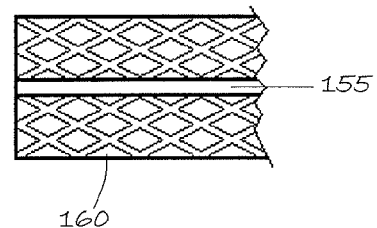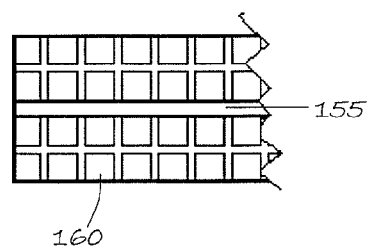

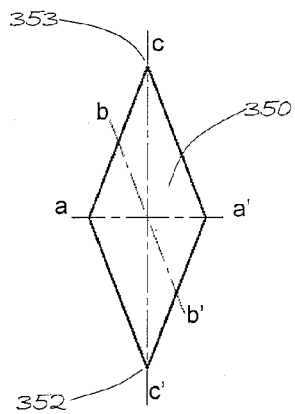 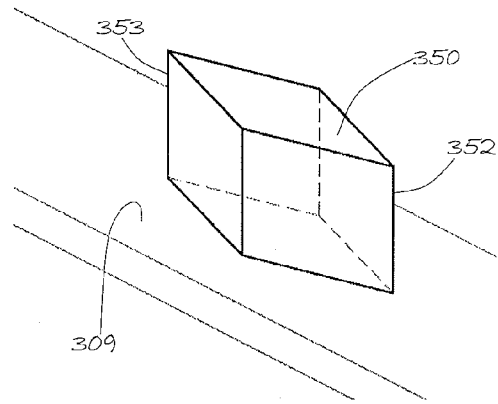
Fig 15a Fig 15b
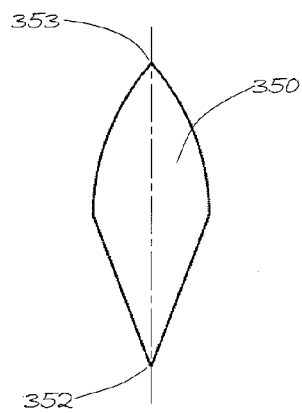 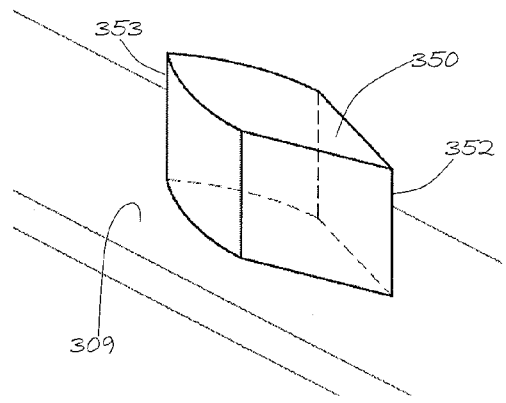
Fig 16a Fig 16b
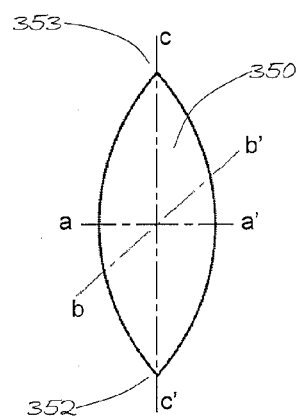 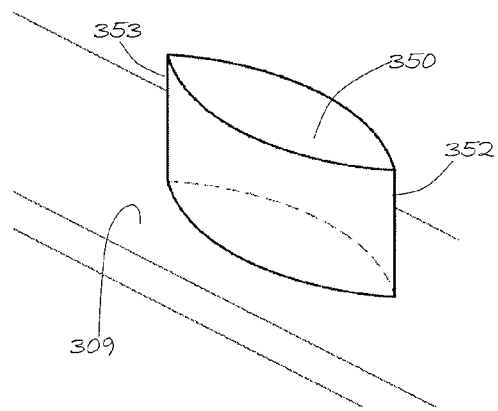
Fig 17a Fig 17b

SIMPLE CAPSULE-BASED INHALER

BACKGROUND OF THE INVENTION

1. Field of the Invention

The present invention describes a re-usable pulmonary or nasal inhaler employing capsules of simple construction and operation and low cost.

Inhalers used for the delivery of pharmaceutical compounds are widely known and they are used for the delivery of several types of medicines treating lung disease and as well as for systemic delivery. Several types of inhalers are known, from those comprising a dosing valve and a pressurized canister invented by Charles Thiel in 1956, to nebulizers and powder-based inhalers. This latter category includes reservoir-based devices, containing a bulk container of powder from which several doses may be dispensed, or a supply of unit-doses packaged in blisters, or simple capsules which are loaded by the patient, cut by the device and which deliver the dose of medicinal powder under the suction of patient's inspiratory effort. The present device is in this last category.

Inhalation delivery presents several technical challenges in relation to oral delivery for buccal, stomach or intestinal absorption, or injection delivery, for the simple reason that the respiratory system is designed to prevent powders, dusts or particles from reaching the lung. In addition, powders with optimal inhalation characteristics namely a very small particle size in the range of 2 to 3 micron in diameter are subject to strong cohesive and adhesive forces which prevent the dose from being adequately dispersed and properly deposited in the bronchi, bronchioles and alveoli. In addition, patient compliance is considerably influenced by the ease of use of the device.

2. Discussion of Background Information

In the field of dry powder inhalers, these challenges have been addressed by two major inventive trends. One has favoured the development of sophisticated and mechanically complex devices and the second prefers a minimalist approach, where simple construction combined with advances in powder technology allows high dispersion leading to high lung deposition and therefore good efficacy, as well as easy use and low cost. We believe this option is the most useful.

The prior art includes many references to capsule-based, re-usable, devices. Indeed Allen & Hanbury's Rotahaler (U.S. Pat. No. 4,889,114) is one early embodiment, with extreme simplicity, but where the delivery performance, particularly the emitted dose, was low and highly variable. Others also described inhalers of the same type, such as GB 1,182,779, Spinhaler; U.S. Pat. No. 4,889,114, Inhalator; FR 75 21844, Cyclohaler; PT 101450; US 2003/131847; WO 2004/082750; WO 2007/098870; WO 2007/144659; WO 2009/139732; US 2009/194105), but the addition of metal cutting means or the necessity to add springs made assembly more complicated and increased cost. More recently, Tsutsui (US 2007/0283955) has proposed very simple inhaler where both ends of the capsule are cut and the domes of the capsule are removed. However, in this design extra components need to be added to prevent the powder from spilling out of the device under gravity and Tsutsui's solution has been to add a valve which blocks this spillage and in use, rises when a suction flow is applied so that air may be admitted to the capsule and disperse and entrain the powder into the mouthpiece. The disadvantage in this invention is that under repeated use, powder will slowly accumulate in the valve mechanism and interfere and ultimately prevent the normal operation of the valve, blocking the operation of the inhaler. Beller (WO 2007/093149) proposes a very similar device. Ideally, inhalers must be simple, deliver reproducible doses and solve the problem of powder interference without resorting to valve mechanisms.

Such interaction between powder, which has a natural tendency to invade mechanical components, and the normal operation of inhalers is impacted by the very fine particle size and increasingly by the dose quantity itself. Whereas the medicines to be delivered by inhalation were typically very potent asthma and emphysema drugs (anti-cholinergics, anti-inflammatory corticosteroids and broncho-dilating beta2-agonists) dosed in the range of micrograms and blended with excipients to achieve total powder doses historically ranging from 5 to 25 mg of total formulated doses, drugs being presently developed for inhalation, such as antibiotics for lung infection, are targeting much higher doses, of 50 to 100 mg of pure drug, to which excipients may then be added. With such high doses, the opportunity for device components to fail because of powder ingress is thus much higher. This means that even if an inhaler has successfully addressed the issue of spilling or leaking powder, it must still be designed to divert and channel out any excess powder which may accumulate under repeated use. This would be benefit.

In terms of the cutting means of the capsule, several designs have been proposed (FR 75 21844; EP 1,245,243; U.S. Pat. No. 6,470,884; US 2007/0283955; WO 2009/117112), but they employ needles or blades which have shortcomings. Most cut the capsule to produce a gaping hole, which allows very good air flow, but does not prevent the powder from spilling out of the capsule immediately prior to use. In any case, air and powder passage holes which are too large provide for a delivery that is too rapid and does not allow the powder agglomerates from becoming successfully dispersed. Consequently, there is the need for an inhaler where the geometry and size of the holes will be sufficiently small to prevent powder spillage, conveniently restrict the passage of air to allow a gradual delivery, effective dispersion and delivery.

In addition, the prior art infrequently refers to the manufacturing method of the cutting means or materials, whereas they have one of the highest impacts on manufacturing cost, on the one hand, and the quality of the cut on the capsule, on the other. In addition, the geometry of the cutting edge is absent from the prior art of inhalers. In this respect, there is the need to develop an inhaler where the cutting means would be optimized for cutting, at the lowest possible cost.

In actuating the capsule, the inhalers of the prior art require a considerable number of steps, due to their mechanical complexity (WO 2007/098,870). The Handihaler inhaler (WO 2009/013218) makes the patient operate the device trough two opening moves, a loading move, a closing move and a piercing move (5 steps) before inhalation. The Cyclohaler inhaler (FR 75 21844) saves on one opening step. There is an opportunity for a device which would only have three steps to inhalation: open, load, close.

The engineering dilemma in such devices is that the inventor is tempted to address operational challenges by increasing the mechanical complexity of the device, detrimentally increasing the complexity of assembly, manufacturing cost, long term reliability and efficacy of the device. The device of the present invention achieves efficiency, reliability, low manufacturing cost and ease of use, by addressing all of the shortcomings identified above. To achieve such a result in a capsule based device with two components only is novel in its own right.

SUMMARY OF THE INVENTION

The present invention provides a dry powder inhaler suitable for pulmonary or nasal delivery, comprising an inhaler body and a capsule tray having a capsule chamber formed therein for carrying a medicament containing capsule. The inhaler body has an inhaler body opening formed therein defined between opposing upper wall and lower wall, said opening having at least one end open by means of which the capsule tray may be engaged into the opening and an inhalation passage which extends through said upper wall and opens into the opening in the inhalation body and an inhalation tube at the other end. Cutting means provided on the upper and lower walls, wherein the capsule tray is moveable engageable in the opening through said open end between a first position in which the capsule tray is withdrawn from the opening to enable a capsule to be loaded into and unloaded from the capsule chamber and a second position in which the capsule chamber is aligned with the inhalation passage in the upper wall and the inlet on the lower wall of the body to enable inhalation of the medicament contained in the capsule through the inhalation passage, the cutting means engaging the top and bottom of the capsule as the capsule tray is moved from its first position to its second position in order to cut openings in the top and bottom of the capsule characterised in that the cutting means are integrated into the inhaler body such that the inhaler is formed of only two operating components.

The dry-powder inhaler of the present invention is intended for pulmonary or nasal delivery, and comprises a first operating component, an inhaler body composed of a mouthpiece or nosepiece, an inhalation inlet, at least two air inlets, an opening for a second component, sliding means to hold in place the second operating component, means to prevent the accumulation of powder, means to limit the movement of the second operating component, means to give tactile feedback to the patient, cutting means and means to allow the patient to see the capsule contained in the second operating component during actuation.

The inhaler comprises a second operating component, a capsule tray, composed of a tray which slides within the inhaler body, means to transport a capsule and hold it in place for proper operation of the cutting means and for inhalation, means to limit its movement inside second component, means to prevent the accumulation of powder and means to give tactile feedback to the patient.

The inhaler comprises a third optional component, a dust cover, which fits over the inhaler body and is designed to prevent dust ingress during storage and transport.

In use, the patient slides the capsule tray in relation to the inhaler body to expose the capsule loading chamber in the capsule tray, loads a capsule, slides the capsule tray so that the capsule travels past the cutting means in the inhaler body, means which slit the capsule extremities and the patient inhales. After inhalation, the patient slides the capsule tray to the original capsule loading position, which is the same as the used capsule removal position, and extracts it.

The inventive elements of the present invention are directed to the inhaler body and to the capsule tray and the fact that the several inventive features of the inhaler are contained within two operating components only is an inventive step hereof.

An operating component is described in this specification as a component which is integral and has no moving parts within it and is essential to the mechanical operation of the inhaler. As the dust cover is not essential to the mechanical operation of the device, being needed for hygiene reasons and regulatory requirements, the present inhaler is said to have at least and no more than two operating components, the inhaler body and the capsule tray.

The inhaler is comprised of a mouthpiece or nosepiece. This is a tube which at one extremity is shaped to enter the mouth or the nose and generally it will have a round or slightly oval section. The internal section of the tube may be round or slightly oval, or any other shape, but its internal wall will preferably be smooth, with no features, cyclones, chambers or corrugations where powder may become trapped. Its internal diameter may be of constant section, or it may vary so that the speed at which air and powder travel through it may be accelerated or slowed down and thus enhance dispersion, entrainment and delivery.

At the extremity of the tube which is away from the mouth, at least one air inlet is provided which admits air to the tube, in sufficient quantity for the patient to have a comfortable inhalation experience. At this end of the mouthpiece, the internal diameter of the inhalation inlet will be just below the diameter of the inhalation inlet, so that the capsule is prevented from surging through the mouthpiece during inhalation.

The inhaler body is provided with an opening which receives a capsule tray. The capsule tray is able to slide inside the opening. This opening is composed of an upper wall and a lower wall, and a front wall and a back wall. Generally, the vertical distance between the upper wall and the lower wall will be determined by the length of the capsule size for which the inhaler is designed. In the case of a number 3 capsule, the specification of which is 15.9±0.30 mm (Capsugel, USA), that vertical distance will be 15.7 mm in the case of one of the inhaler embodiments of the present invention. The internal walls of this opening will generally be flat and smooth, so as to allow the capsule try to be inserted in it, and to allow the patient to move the capsule tray sideways. In order to better control the sliding motion of the capsule tray, the inhaler body may be provided with a rail mechanism, which will mate with a corresponding slot in the capsule tray.

The internal walls of the opening may be provided with small interferences on the surface, placed in the path of the movement of the capsule tray, which will produce a clicking sound or tactile feeling to the patient during the movement of the capsule tray, to indicate that the inhalation position has been reached. The inhaler body opening is provided with means to limit the travel of the capsule tray and prevent the patient from pushing the capsule tray out of the inhaler body through excessive force or movement. Such interferences and mechanical blocks are common features of mechanical devices.

The inhaler body is further provided with two air inlets, which are aligned with the longitudinal axis of the mouthpiece or nosepiece: the inhalation inlet previously mentioned and an air inlet which, when the capsule is in the inhalation position, admits air to it.

The inhaler body has cutting means, composed by two blades which are anchored in the upper and lower internal wall of the inhaler body opening. The blades are disposed so that their cutting edges are perpendicular to the upper and lower internal walls and aligned along the same plane. Therefore the edges of the blades are in alignment and this alignment is parallel to the longitudinal axis of the loaded capsule. The blades protrude from the upper and lower internal wall a small height, generally 2 mm or less when using number 3 conventional pharmaceutical capsules, so that the cutting action will be limited to the extremities of the capsule in use and both ends will be neatly slit. The inhaler may be designed for other sizes of pharmaceutical capsules, in which case the blade heights will have to be adjusted to provide for cuts of adequate size, as determined by experimentation. Generally, we prefer that the height of the blade located in the lower internal wall in the body opening be less than the blade located in the upper internal wall, so as to produce a smaller cut in the capsule and prevent the powder from spilling or leaking. In the case of a number 3 capsule, we prefer to dimension the height of the lower wall blade between 1.0 and 1.6 mm and the height of the upper wall blade between 1.4 and 2.0 mm. These slits will be very narrow, advantageously preventing the powder from spilling out of the capsule after the capsule has been cut. Moreover, since the material of the capsules is somewhat elastic, the slits tend to narrow again after the blades have cut through the capsule.

These blades may be made of metal, such as stainless steel, the most appropriate grades being of surgical purpose quality. When using an inhaler body made of plastic, one of the adequate manufacturing techniques is insert-moulding during the injection-moulding process, so that the blades and the inhaler become one integral component. Alternatively, the blades may be made of the same plastic as the inhaler body, and be formed in the same injection moulding cycle, again resulting in one integral component but of much lower manufacturing cost. Cutting means of the same material as the inhaler component into which they are anchored are novel and an inventive step in the present invention. Plastic blades used in an inhaler as cutting means are an important feature of the invention.

When using plastic blades or blades of the same material as the inhaler body, the grade of plastic used must be desirably be very hard, so that the quality of the edge may survive repeated cutting actions without loss of cutting performance. When manufactured by injection moulding, the design of the mould must be such to avoid the formation of flash, a moulding imperfection where an irregular film of plastic material extends from the cutting edge thereby diminishing the quality of the cut, or altogether preventing it. Mould designs can contain an action composed of mould components which shut to form the shape of the blade as plastic polymer is injected, or they can form the blade through an integral mould, without a moving action.

Blades made of the same material as the inhaler body means that this latter component is manufactured in a single or unitary step to mould the blades as well, so that the inhaler body includes blades as an integral feature, and this is a further inventive step of the present application.

An additional inventive step is that the blades are double-edged. In other words, each blade of this inhaler comprises two edges, so that they may cut the capsule in both directions when the capsule tray is pushed forward inside the inhaler body towards the inhalation position, and cut again when the capsule tray is pushed or retracted in the opposite direction. This second cut is not needed for the inhalation manoeuvre, but only to allow a comfortable movement of the capsule tray after inhalation, when the patient brings the capsule tray to the open position to remove the used capsule. In the most preferred embodiment, this movement necessarily brings the used capsule again in contact with the blade, in the opposite side of the first cutting edge. If the blade was not provided with a cutting edge and was instead blunt, the extremities of the inhaled and empty capsule would be crushed by the movement and it might become difficult to remove. The second cutting edge provides for a smooth movement past the blades. In another less preferred embodiment, the capsule removal position occurs at the opposite side of the initial loading position. In this case, the capsule tray moves always in the same direction, as it is loaded with a capsule and is pushed to the inhalation position and then to the removal position, on the opposite side of the inhaler body. In this embodiment the blades do not require a second edge as the capsule does not travel back across them.

An additional inventive step of the doubled edged blades concerns their section. The blade section can be a lozenge, with a blade at each of the apexes of the lozenge and this type of blade section in a capsule-based inhaler is new. In this design, the blade section is composed of four straight sides and the design is symmetrical along any line drawn through the centre of the blade section. Such a blade design used in capsule-based inhalers is new. For manufacturing reasons, there may be a need to extend the length of the blade, so that its section in fact has six sides, where two sides are parallel and form the middle section of the blade, and each edge extending from that middle section has a triangular shape.

The blade section can also be formed by two arcs of circle and the two blade edges are defined by the intersection of the two arcs. In this design, the blade section is composed of two curved sides and the design is symmetrical along any line drawn through the centre of the blade section. Such a blade design used in capsule-based inhalers is new.

The two designs may be combined, so that the blade may have one edge composed of two straight sides, and the other of two curved sides and this combination may be used to provide a better quality of initial cut and of exit cut or optimal slit width on the capsule. Such a blade design used in capsule-based inhalers is new.

In a side view, the double-edged blade is square or rectangular, so that when the capsule touches the blade edge, there is a reduced area of contact which promotes cutting and reduces the probability of the capsule becoming crushed. A square or rectangular side view shape of double-edged blades are novel and constitute an inventive step of the present application.

The second operating component of the inhaler is the capsule tray, which is intended to fit inside the inhaler body and slide within it between the open and closed position. The capsule tray comprises four sides dimensioned to fit closely in the inhaler body opening, namely an upper wall, a lower wall, a front wall and a back wall. The front wall comprises a capsule chamber and its function is to receive the capsule containing a unit dose of pharmacologically active powder. The capsule chamber may be a cylinder, so that the capsule will be loaded from the top, but preferably it will be a half-cylinder and in both cases it will be wider than the capsule so that the latter may move freely lengthwise in the capsule chamber.

In one embodiment, the capsule tray may be provided with a handle to enable an effective grip by the patient and in this case the capsule tray will be pulled out to the open position to receive a capsule. In another embodiment, the capsule tray is intended to be pushed into the inhaler body, so that the capsule chamber is revealed on the opposite side of the inhaler body.

In order to prevent the accumulation of powder the upper wall and the lower wall may comprise features to prevent such an accumulation. These features are integrally moulded with the capsule tray, but they may also be moulded in the adjoining inhaler body internal upper and lower walls. However it is preferable to mould them with the capsule tray. These upper and lower walls will be of an uneven surface textured, corrugated or contoured with hemispheres, grooves, channels or ridges and they may be disposed to form a grid of perpendicular or oblique lines, in relation to the edges of the capsule tray, or a chevron pattern, or tire pattern or combinations thereof. In this manner powder trapped between the inhaler body and the capsule tray will not accumulate at the points of contact between the two components and will instead be diverted along the channels of the ridges, thereby improving the smoothness of the capsule tray moving inside the inhaler body. Such features to prevent the accumulation of powder are an advantage in re-usable powder inhalers and constitute and inventive step in this specification.

These components can be made by injection-moulding and use any grade of pharmaceutically suitable grade such as PolyCarbonate (PC), Polypropylene Oxide (PPO), Polybutylene Terephthalate (PBT) Polyethylene Terephthalate (PET), LCP Liquid crystal polymer, Polyethyleneimine (PEI), Polyphenylenesulphide (PPS) Polyethylene (PE) Polypropylene (PP), Polysulfone (PSU), Acrylonitrile butadiene styrene (ABS), polymethylmetacrilate (PMMA). The polymer can be natural or glass filled. However, when the blades are injected-moulded together with the inhaler body, they will be made of the same material and a hard plastic material is preferred. Grades such as PC, PPO, PBT, PET glass filled, PPS, PSU, ABS are indicated.

Useful capsules for the inhaler of the present invention include conventional pharmaceutical grade capsules, made of gelatine or cellulose/HPMC, of any size, such as size number 3, or any other size. They can also include custom-designed capsules, made of any other suitable material.

In use, the patient only requires three inhaler movements to prepare the inhaler for inhalation, open, load and close. Many inhalers of the prior art require four inhaler movements to prepare the inhaler for inhalation, open, load, close and cut. Saving one step is a benefit for the patient, makes for a simpler inhaler during operation and leads to better compliance.

In use, the patient holds the inhaler body and slides the capsule tray to expose a capsule loading chamber. This is the open position of the inhaler. A capsule containing a pharmacologically active drug, suitably formulated for inhalation, is then loaded into the chamber by the patient.

The patient then slides the capsule tray in the opposite direction and this movement takes the capsule past the blades anchored in the upper and lower internal wall of the inhaler body where both capsule extremities are cut, forming a thin slit and substantially no capsule material is removed by the cut. The patient continues to push the capsule tray until the capsule is aligned with the mouthpiece. Advantageously the internal walls of the inhaler body and the surface of the capsule tray may be provided with interference features which sound an audible and tactile click, indicating to the patient that the inhalation position has been reached. The inhaler is now in the closed position and is ready for inhalation.

The patient exhales to empty the lungs of air, brings the inhaler to the lips or nostril and inhales. The movement of the powder may be viewed if a transparent capsule is used, through the window on the capsule body at the inhalation position. After inhalation, any remaining powder is clearly visible and if that is the case, the patient may repeat the inhalation until all powder has been delivered.

The suction applied to the mouthpiece causes a pressure drop across the inhaler, the intensity of which is a function of the inspiratory effort generated by the patient and by the resistance to the passage of air caused by the air pathways inside the inhaler. This resistance is primarily governed by the section of the air inlet or inlets on the inhaler body and secondarily by the surface of the slits on the cut capsule. In the inhaler of the present invention, when a cut capsule is in front of inhalation inlet so as to block it, the nominal pressure drop is 4 kilopascal at an airflow rate of 35 liters of air per minute. Pressure drops as low as 2 kilopascal may still deliver a full emitted dose under compendial testing conditions, when using appropriate powder formulations, as the inhaler is particularly efficient at low air flow rates.

When the inhaler is in the closed position, the cut capsule is aligned with the mouthpiece. As an inspiratory effort is applied, the air flow and the pressure drop cause the capsule to move forward inside the inhaler body capsule chamber until it blocks the inhalation inlet at the bottom of mouthpiece tube. Since the internal diameter of inhalation inlet is less than the diameter of the capsule, the dome of the capsule which is slit enters the inhalation inlet and effectively blocks it, so that air is forced to enter the capsule through the slit in the opposite capsule extremity. The air entering the capsule through this lower slit is admitted via an inlet in the inhaler body lower internal wall, or via air leak passageways between the capsule body and the capsule tray. The air surging through this lower slit enters the capsule, aerosolizes the powder and entrains it through the upper capsule slit, into the mouthpiece tube, out of the mouthpiece, into the patient's mouth or nose and then to the intended zone of deposition in the respiratory system.

When the inhalation manoeuvre is concluded, the patient slides the capsule tray towards the open position, and removes the used capsule. The patient returns the capsule tray to the closed position and replaces the optional dust cover.

The purpose of this inhaler is the delivery of pharmaceutical substances to the body, via the nose or the lung, to treat diseases locally or systemically. Useful drugs are beta2-agonists (e.g. salbutamol, levalbuterol, pirbuterol, procaterol, formoterol, eformoterol, salmeterol, terbutaline), anti-cholinergics (e.g. ipratropium, tiotropium), anti-muscarinics, corticosteroids (e.g. fluticasone, beclomethasone, budesonide, ciclesonide, mometasone, flunisolide, triamcinalone), cromoglycate and nedocromil, steroid modulators, anti-infectives (e.g. tobramycin, fosfomycin, doxycycline, amikacin, pentamidine, zanamivir, laninamivir, other neuraminidase inhibitors), analgesics (e.g. fentanyl, ergotamine, sumatriptan), proteins/peptides (e.g. insulin, dornase alfa, leukotriene inhibitors), SiRNA compounds, erectile dysfunction drugs (e.g. apomorphine), anti-hypertensives (e.g. iloprost), smoking cessation agents (e.g. nicotine), lung cancer drugs and compounds having both a broncho-dilating and an anti-inflammatory activity.

BRIEF DESCRIPTION OF THE DRAWINGS

In order that the invention may be well understood, there will now be described some embodiments thereof, given by way of example, reference being made to the accompanying drawings, in which:

FIG. 5 is a side view of the inhaler body of FIG. 1 showing the inhaler body opening and the cutting means provided therein;

FIGS. 6 and 7 are end and perspective views of the capsule tray;

FIGS. 8a to 8c are partial top views of the capsule tray of FIG. 2 showing surface finishing thereof according to 3 different embodiments;

FIGS. 15a and 15b are top and perspective views of one blade shape;

FIGS. 16a and 16b are top and perspective views of a second blade shape;

FIGS. 17a and 17b are top and perspective view of a third blade shape.

DETAILED DESCRIPTION OF THE INVENTION

Figure 1:
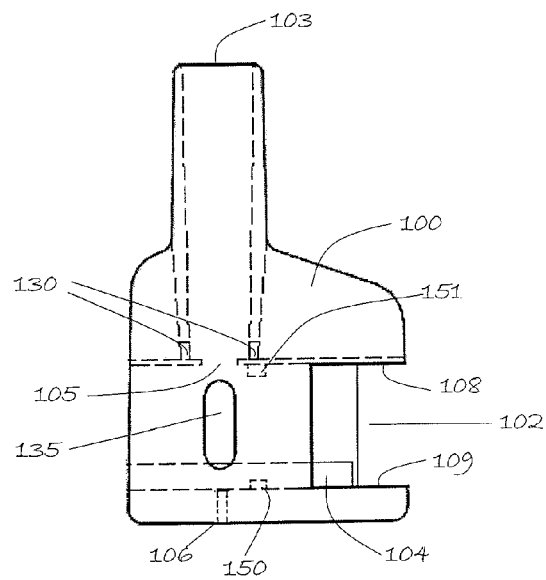
FIG. 1 is a side view of an inhaler body according to the invention.

All of these embodiments comprise the inventive features detailed in the present application and the person skilled in the art will be able to apply the same teachings to other inhalers so these descriptions in no way limit the invention to the embodiments described.

Referring to the drawings, numbered sequentially after the word "FIG.", like numerals indicate like parts, and each of the three embodiments is identified with series of numbers where the number of hundreds is the number of the embodiment (1xx to 3xx) and the equivalent feature in each of the embodiments has the same number xx.

Referring first to FIG. 1, there is shown an inhaler body 100 which forms one part of a two part inhaler assembly according to the invention.

The inhaler body 100 has an opening 102 formed therein for receiving a capsule tray 110 as described below, the opening being bound at the top and bottom by opposing upper 108 and lower 109 walls. An inhalation passage 105 extends from the upper wall 108 of the opening to a mouthpiece 103 located at the top of the body 100 so as to provide fluid communication between the opening 102 and the mouthpiece 103. An air inlet 106 is also formed in the lower wall 109 which extends from the opening 102 to the bottom of the body 100 so as to provide fluid communication through the lower wall 109 into the opening 102, thereby establishing a fluid flow path from the outside of the lower wall 109, through the opening 102, into the inhalation passage 105 and to the mouthpiece 103.

Figure 2:
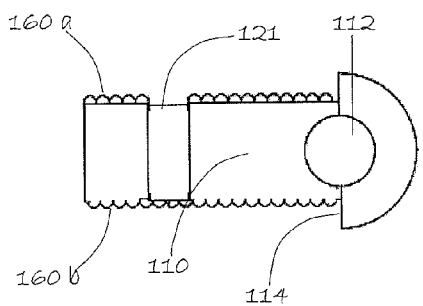
FIG. 2 is a side view of a capsule tray which engages with the inhaler body of FIG. 1.

The capsule tray 110, shown in FIG. 2, is sized and shaped to be moveable engageable in the opening 102 in the inhaler body 100 for enabling inhalation of a powder contained in a capsule mounted therein. The body 100 includes a rail 104 on the lower wall 109 which co-operates with a complementary shaped rail stop 124 formed on the back of the capsule tray 110, as best shown in FIG. 6, the rail stop 124 cooperating with the rail 104 and a stopping element 114 so as to limit the movement of the capsule tray into the opening 102 and thereby ensure correct alignment of the capsule with the inhalation passage of the body 100 as described below. An engagement mechanism may also be utilized between the rail and the rail stop which gives the operator an audible and/or tactile indication that the capsule tray 110 has reached its fully inserted position. The design and configuration of such a mechanism is well within the knowledge of the skilled person and will not be described here in any detail. A handle 112 is also formed in the end of the capsule tray 110 to enable a user easily to engage and withdraw the tray from the body 100.

The upper and lower walls 160a and 160b of the capsule tray 110 are preferably textured so as to prevent the build up of powder thereon which could inhibit the sliding movement of the capsule tray 110 into and out of the inhaler body. They may also be configured to interface with the upper and lower walls 108, 109 of the inhaler body in a ratchet fashion in a manner which is well known to the person skilled in the art.

A capsule chamber 121 is formed in the tray 110 which is sized and shaped to hold a powder containing capsule 123. The chamber 121 is dimensioned to receive a capsule 123 and its lower end may be narrower than the capsule width to prevent the capsule 123 from dropping out of the chamber 121 when the tray is withdrawn from the body 100.

Figure 3:
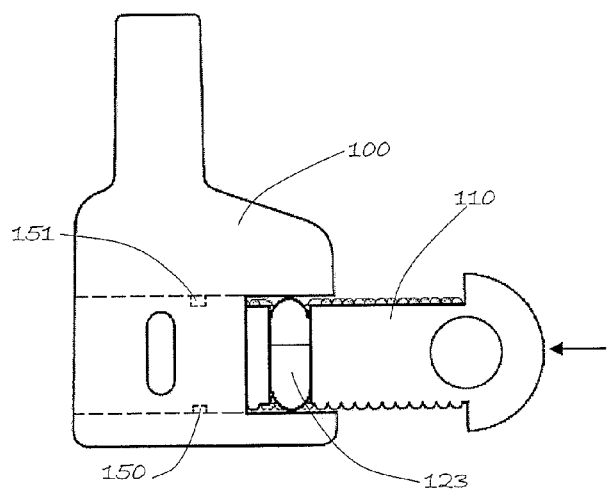
FIG. 3 is a side view of the capsule tray of FIG. 2 partially engaged with the inhaler body of FIG. 1 in a first, load position.
Figure 4:
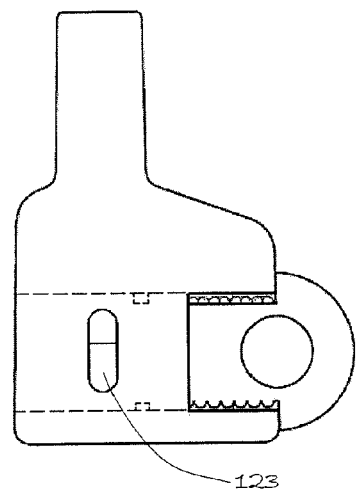
FIG. 4 is a side view of the capsule tray of FIG. 2 fully engaged with the inhaler body of FIG. 1 in a second, closed position.

The capsule chamber 121 is sized so that the capsule 123 is a loose fit therein, facilitating insertion and removal of the capsule from the chamber and also enabling the capsule to move within the chamber during use as described below. In this embodiment, the chamber 121 is furthermore shorter than the capsule 123 so that the top and bottom of the capsule project above and below the upper and lower walls 160 of the capsule tray 110 as shown in FIG. 3. Furthermore, when closed by the inhaler body, the chamber 121 is sized to provide lateral and longitudinal support to the capsule so that when the tray is moved by the user towards the inhalation position, the passage through the cutting or piercing mechanism (150, 151) causes cuts that are precise and reproducible in repeated use. Although a degree of lateral movement is permissible, that should be restricted.

The capsule chamber 121 is positioned on the capsule tray 110 such that when the tray is fully inserted in the opening 102 in the body 100 with the rail stop 124 engaged with the rail 104, the chamber 121, and hence any capsule 123 mounted therein, is aligned with the inlet opening 106 and inhalation passage 105 of the inhaler body 100.

The capsule 123 which is inserted into the capsule tray 110 will be sealed and the body is therefore provided with cutting means 150, 151 for cutting or piercing both the top and the bottom of the capsule in order to enable air to be drawn there through during operation. As shown in FIG. 1, the cutting means 150, 151 comprises a pair of blades 150, 151, one of which extends from the lower wall 109 into the opening 102 for piercing the bottom of the capsule 123, and the other of which extends from the upper wall 108 into the opening for piercing the top of the capsule 123. As shown in FIG. 5, each blade 150, 151 is oriented with its cutting edge extending substantially vertically from the wall on which it is mounted towards the opposing wall. In this way, as the tray 110 is pressed into the body 100, the blades cut a narrow slit across the top and bottom of the capsule 123 to enable a passage for air to be sucked through the capsule during use and the powder contained therein to become dispersed inside the capsule, entrained out of it and inhaled through the mouthpiece 103. FIG. 5 also show air inlets 130 which admit most of the air being drawn through the inhalation tube, as the amount of air travelling though the slits on the capsule is reduced, due to their small size and there is a need to add more air to allow the patient to inhale comfortably. Additional air admitted via air inlets 130 will also increase the turbulence as the powder exits the capsule and enters the mouthpiece via the inhalation inlet 105, contributing towards the deaggregation of powder agglomerates.

The height of each blade 150, 151, that is the distance it projects beyond the wall with which it is associated, is greater than the clearance between the walls 108, 109 of the opening 102 and the capsule tray 110. This is to ensure that a appropriate slit is cut in the capsule 123 and hence good airflow can be achieved there through. In order, then, to enable the tray to move into the opening past the blades, a longitudinally extending slot 155 is formed in both the top and bottom of the tray 110 in alignment with the blades such that when the tray 110 is inserted into the opening, the blades 150, 151 engage in the slot 155 and are guided into engagement with the top and bottom of the capsule 123. This configuration has the further advantage that the capsule is supported on either side of the cutting location, thereby making the cutting operation more reliable.

As shown in FIG. 1, the inhaler body 100 preferably has a window slit 135 formed in its side wall 107 in alignment with the air inlet opening 106 and inhalation passage 105. The tray 110 is also preferably open at one side of the chamber 121 corresponding with the side in which the window slit 135 is formed in the body 100 so that, when the capsule 123 is in its inhalation position within the body 100, it is visible through the window 135. This enables a patient or carer to check that the capsule is in its proper place for inhalation and whether the entire contents of the capsule have been inhaled.

Figure 9:
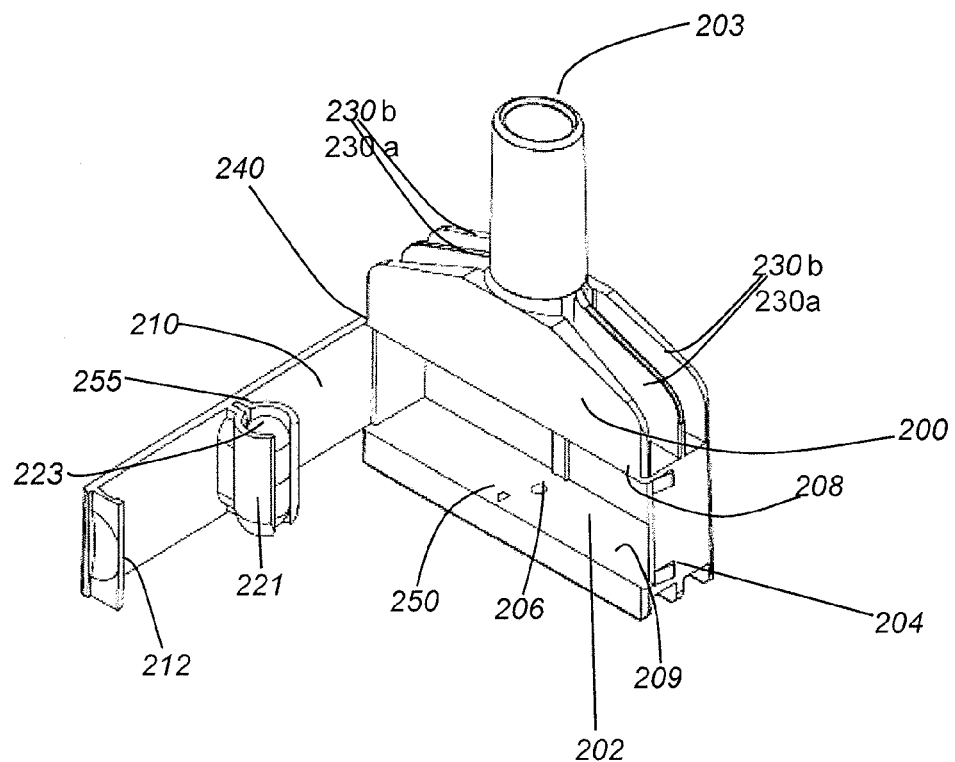
FIG. 9 is a perspective view of a second embodiment of the invention.
Figures 10A, 10B, 10C:
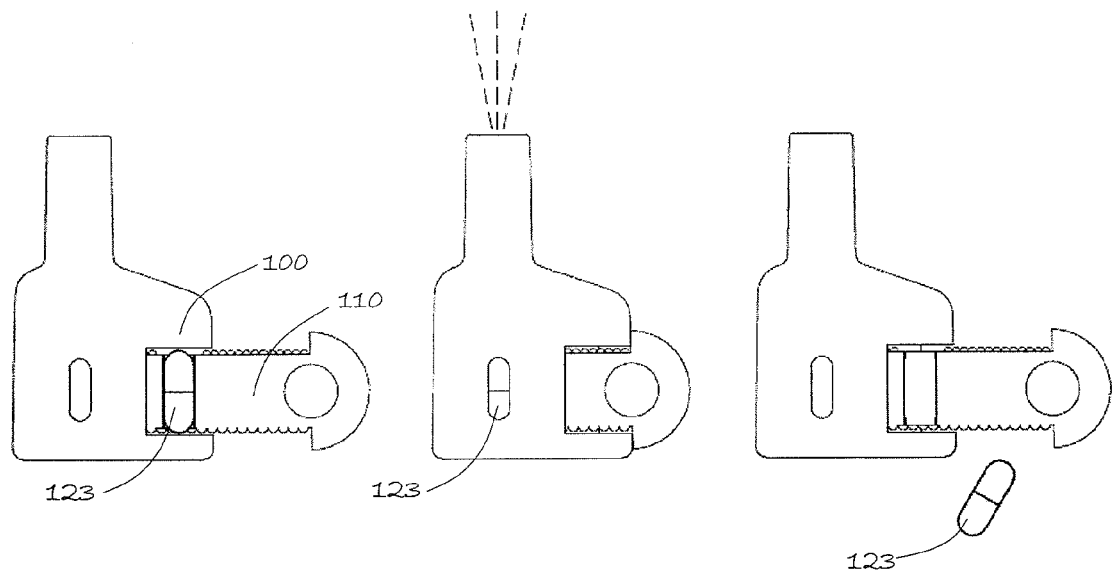
FIGS. 10a to 10c are the inhaler according to the first embodiment of the invention in 3 different operational positions.
Figure 11:
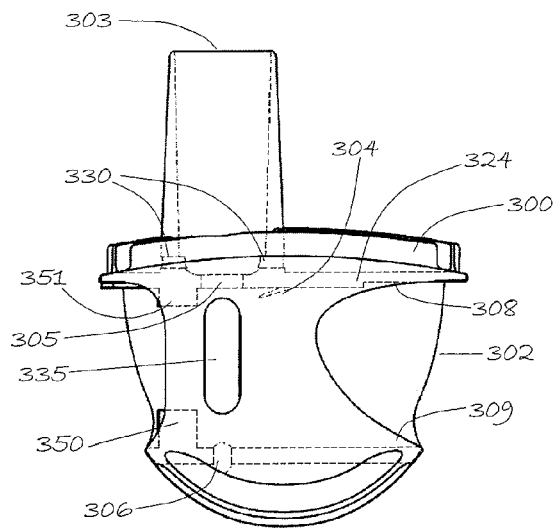
FIG. 11 is a view of an inhaler body according to a third embodiment of the invention.
Figure 12:
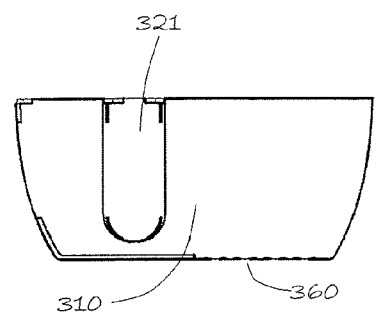
FIG. 12 is a view of a capsule tray which engages with the inhaler body of FIG. 11.
Figure 13A:
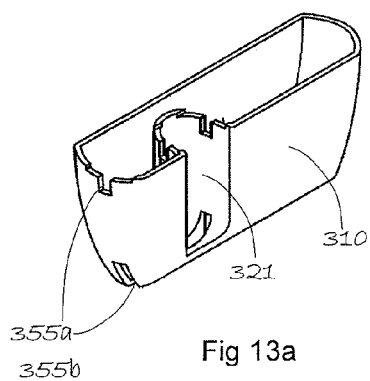
FIGS. 13a to 13c are perspective and end views of the capsule tray.
Figure 13B:
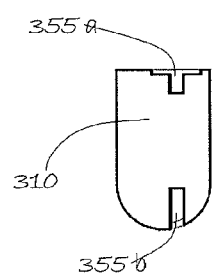
Figure 13C:
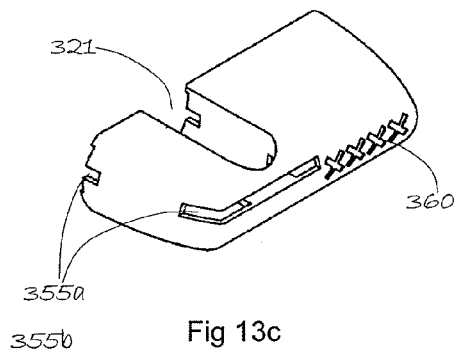
Figure 14A:
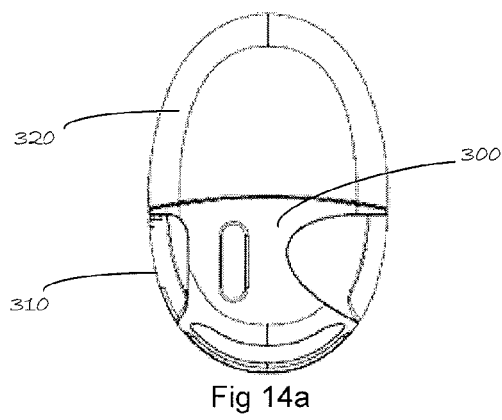
FIGS. 14a to 14h illustrates the operational steps to open, load, inhale and unload the inhaler.
Figure 14B:
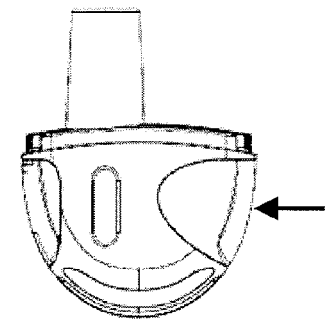
Figure 14C:
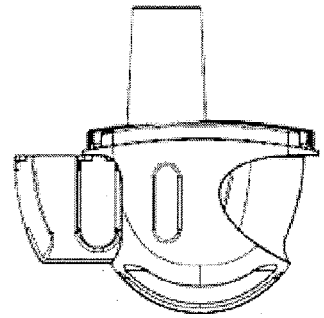
Figure 14D:
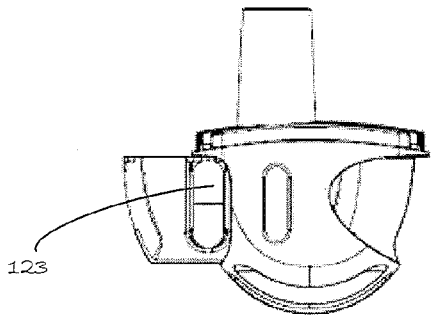
Figure 14E:
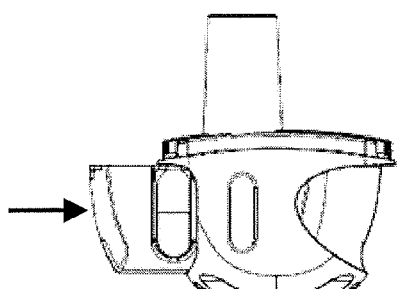
Figure 14F:
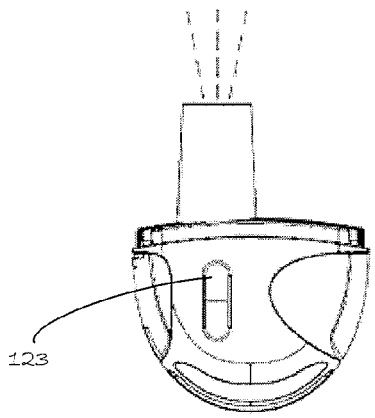
Figure 14G:
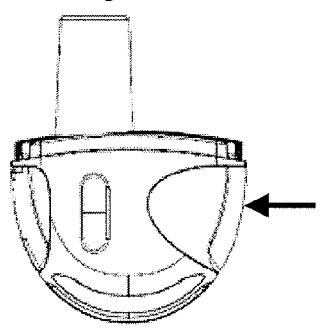
Figure 14H:
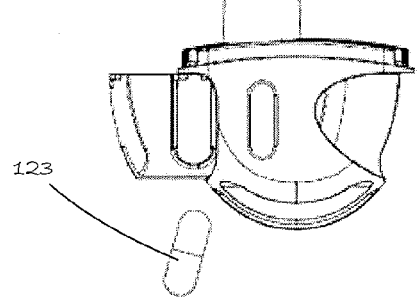

FIG. 9 shows an alternative embodiment of the invention in which the movement of the capsule tray relative to the inhaler body 200 is pivotal rather than linear—the tray 210 being pivotally mounted to the body 200 for movement between an open position shown in FIG. 9 for loading and unloading of the capsule 123 from the chamber 221, and a closed position in which the capsule is positioned for inhalation of the contents thereof. Cutting blade 250 and a blade not shown but corresponding to blade 151 in FIG. 3 are provided in positions appropriate to interface with the top and bottom of the capsule as the tray 210 is moved into its closed position and thereby cut a slit in the top and bottom of the capsule. Like features of the first embodiment are identified in this second embodiment by the same reference numeral increased by 100.

Although FIG. 9 shows the axis of rotation 240 of the capsule tray at the end of the inhaler body, it will be understood that it can, in fact, be anyway along the body as long as it does not align with the inhalation passage 205 and air inlet opening 206.

FIGS. 11 to 14h show a third embodiment of the invention in which features in common with the first embodiment are identified using the same reference numerals increased by 200. The configuration and operation of this embodiment is identical to that of FIG. 1 except that the opening 302 in the inhaler body 300 is open to both sides of the body 300 so that the tray 310 can be engaged from either side of the body 300. In this way, a handle is no longer required on the tray 310 as movement of the tray in both directions can be effected by pushing the tray in either direction from either side of the body as shown, in particular, in FIGS. 14b and 14e. In this embodiment, the capsule is still inserted into and removed from the tray 310 the same position, but it is instead possible that the tray may be moveable completely through the opening so as to enable the capsule to be inserted into the tray on one side and removed on the other.

In one other possible embodiment which is not illustrated, the capsule tray may be configured for rotational movement about an axis which is perpendicular to the mouthpiece tube.

FIGS. 15a, 16a and 17a show a section view of three embodiments of novel double-edged blades of the present invention and FIGS. 15b, 16b and 17b show corresponding perspective views of the same blades. In these drawings, the width of the blade is given by line aa', the length by line bb' and the blade section is symmetrical along any line drawn through the section thereof, such a line cc'. The blade 350 has two cutting edges 352 and 353. The blade embodiment of FIG. 17a is a hybrid of the embodiments of FIGS. 15a and 16a. These blades 350 are shown anchored to the lower wall 309 of the inhaler body and the manner in which they will be disposed in the upper wall of the inhaler body is the same.

The inhaler is intended to be re-usable. Inhalers employing plastic or ceramic blades are novel. Re-usable inhalers employing plastic or ceramic blades are novel. The inhaler of the present invention is intended for one month's use, for one, two or three capsules per day. Therefore it is intended to be used 30, 60 and up to 90 times.

The device is operated as follows:

The tray 110 is withdrawn from the inhaler body 100 so as to expose the chamber 121, and a new, sealed capsule 123 is loaded into the chamber 121. The tray 110 is then slided firmly back into the opening 102 in the inhaler body 100 until the rail 104 is engaged with the rail stop 124. As the tray moves into the opening 102, the blades 150, 151 travel along the slots 155 in the tray and cut slits in the top and bottom of the capsule.

The user then places the mouthpiece 103 into his or her mouth or in a nostril of the nose and air is then inhaled through the mouthpiece 103. The resulting pressure drop in the inhalation passage 105 firstly sucks the capsule into abutment against the inhalation passage opening in the upper wall 108 of the body opening 102. The inhalation passage opening 105 is sized to be smaller than the width of the capsule 123 and the capsule cut is substantially exposed to the inhalation passage 105. The top end of the capsule also forms a seal with the surrounding upper wall 108 of the opening 102. With this seal preventing air from entering the inhalation passage 105 except through the capsule slits, the suction applied by the patient then draws air through the inlet opening 106 in the lower wall 109 of the inhaler body 100, through the capsule 123 by means of the slits cut therein by the blades 150, 151 and into the inhalation passage 105. As the air travels through the capsule, it aerosolizes and disperses the dose of medicament powder it contains, entraining it out of the capsule, into the inhalation passage, and finally into the mouth or nose for final delivery at the desired location of the body of the user.

The patient or carer can then check whether the full dose has been inhaled by using the window 135 in the body 100 to check for any powder remaining in the capsule. Once he is satisfied that the full dose has been administered, the tray 110 is withdrawn from the body 100 and the empty capsule disposed of, leaving the inhaler ready for re-use.

When the user reaches the unloading position, a mechanism may be utilized which provides an audible or tactile warning, indicating that the position has been reached, or alternatively further motion is blocked, by means of mechanical elements The operation procedures for the third embodiment of the inhaler of the present invention are described in detail in FIGS. 14a to 14h.

As discussed above, surfaces in contact with the capsule tray, particularly in the guides, are preferably textured or have a configuration suitable to prevent or reduce powder accumulation in such areas of contact. This may be achieved by an uneven surface in the inhaler body upper and lower walls, or with a surface provided with a mechanism to sweep or scrape the powder when the movable tray is moved; or a blowing system to remove powder from the interference between body and the movable tray; or a vacuum system to draw the powder which is in the space between the body and the movable tray; or a gap between body and movable tray which avoids powder retention between the two components; or any combination of such features. In the preferred embodiment, the surface on one contact area (or both of them) is corrugated, for example with one of a wave pattern, a spherical pattern, a square pattern, a criss-cross pattern, a parallel line pattern, a chevron pattern, a tire pattern, or any geometric pattern capable of preventing or minimizing the build-up of powder in areas of interface between device components (examples shown in FIGS. 8a to 8c). The tendency is for powder residue to accumulate on the walls 108, 109 of the body, interfering with the smooth movement of the tray into and out of the opening. The provision of the textured surfaces on the capsule tray has the effect of helping to dislodge any residue powder from the confronting surfaces of the body by a scraping action, significantly reducing the build up of powder residue and hence reducing the instance of jamming of the tray in the opening over prolonged use.

Although the cutting elements have been described above as being blades, alternative means are also possible such as claws or needles. The cutting means may be made of metal, plastic, ceramic or any other material which is compatible with a pharmaceutical function and the mechanical requirements of inhalation. The cutting edge may have a pointed or rounded tip, but the design is configured to achieve a smooth cut, without producing capsule debris, that is without removing any portion of the capsule 123 such as a top portion thereof as is done in prior art systems.

Examples of different blade designs and configurations for the cutting means are shown in FIGS. 15a to 17b.

In the preferred embodiment, the cutting or piercing mechanisms are integrated into the body 100 of the inhaler. In particular, the cutting elements 150, 151 are preferably manufactured, formed or moulded with the body in one piece, but can alternatively be inserted during manufacture of the body, or after its manufacture. In particular, the cutting or piercing elements are preferably formed in the same manufacturing step as the body 100, using the same material for body and cutting or piercing elements, so that such elements are an integral part of the body 100. The manufacturing process may employ the same material for both body and piercing or cutting elements, or different ones, such as metals or ceramics, if one material is more appropriate for the body function and another is more appropriate to the cutting or piercing function, but the important thing is that they both be manufactured, formed or moulded in the same common manufacturing step. A same or common manufacturing step is defined here as an operation taking place inside the same manufacturing equipment, during the same complete manufacturing cycle. This results in a lower manufacturing unit cost.

The cutting blades 150, 151 are then formed with the necessary cutting surface so that no further manufacturing or finishing step is necessary. However, further manufacturing steps, such as sharpening, conditioning, heat treating, cold treating, chemical treating, abrading, eroding, corroding or coating, may also be applied in order to increase mechanical integrity and fineness, sharpness, resilience and resistance of the piercing or cutting edge or of the element itself.

The inhaler may also have a cover 320 (shown in FIG. 14a) that serves to close the mouthpiece, thus preventing the accidental entry of dust and particles during storage. The cover may be integrally formed with the body 300 so as to be moveable relative thereto or may be a separate element. In the storage position, the cover closes the mouthpiece and protects it. The cover can be connected to another component of the inhaler, or have no tie.

The capsules can be of any material, i.e. gelatine, cellulose, plastic or any other that is pharmaceutically compatible with the drug. The capsule employed may be of any size, for example 00, 0, 1, 2, 3, 4 and 5 and the size of the inhaler, of the inhaler body, of the capsule tray and of the capsule chamber will be a function of the capsule size. The inhaler will be sized to fit comfortably inside a chamber, and to fit conveniently in one hand.

To ensure smooth movement of the tray 110 during removal of the spent capsule, the cutting blades are preferably double edged so that they cut through the material of the capsule as it is withdrawn from the body. This prevents the possibility of the backs of the blades catching on the capsule as it is withdrawn, which could cause jamming of the mechanism. Alternatively, however, the mechanism could be configured for spent capsule to travel on through the opening in the body for removal, in which case a second pair of cutting blades may be provided on the other side of the inhalation passage 105 again for helping to prevent jamming of the assembly during removal.

EXAMPLE

An inhaler embodiment of the present invention has been tested to determine its aerodynamic profile as well as its powder dose delivery. An experimental lactose based blend comprising tiotropium at a dose of 18 micrograms per capsule was then formulated to determine the dispersion and the entrainment efficacy of the inhaler.

After blending of the formulation components to produce an ordered mix and determining the batch homogeneity, the formulated powder was filled into cellulose HPMC capsules, size 3 (Capsugel, USA) to be used in the device of this specification. The inhaler was then tested at a flow rate of 35 liters per minute and a pressure drop of 4 kPa on a Next Generation Impactor (Copley Scientific, UK), actuated twice to allow a volume of 2×2 liters of air to pass through the device and the mass of active drug deposited at each stage of the cascade impactor was quantified using high pressure liquid chromatography. From these data, the emitted dose and the fine particle dose were calculated, where the emitted dose was the sum of all drug masses collected from each of the impactor stages, including the inductor throat, and the fine particle dose was the mass of drug collected below the 5 micron cut-off point. The ratio of the fine particle dose to the emitted dose is the fine particle fraction and is a measure of inhaler efficiency. The higher the fine particle dose, the higher the lung dose is expected to be. The results are summarized in the following table

|  | Delivery performance |
|---|---|
| Emitted dose ED | 14.2 mcg |
| Fine particle dose FPD | 5.1 mcg |
| Fine particle fraction (ED/FPD) | 36.0% |

These data indicate that the inhaler of the present specification is capable of effectively delivering a dose of an inhalation drug, under inspiratory effort conditions which are compatible with the ability of patients.

The invention claimed is:

1. A dry powder inhaler suitable for pulmonary or nasal delivery containing only two operating components each of which is integral, each of said components has no moving parts within it, and each of said components is necessary for the mechanical operation of the inhaler, said operating components being an inhaler body and a capsule tray;

the inhaler body having opposing upper and lower walls defining an inhaler body opening between said opposing upper wall and lower wall, an inhalation passage extending from the inhalation body opening through said upper wall, an inhalation tube extending from the inhalation body opening through said lower wall, first and second cutting elements fixed and integrated on said upper and lower walls, respectively, and disposed to cut openings in adjacent portions of a capsule as the capsule is moved past the cutting element by the capsule tray, and said inhaler body opening including an open end adapted to permit the capsule tray to be engaged into the inhaler body opening;

the capsule tray having a capsule chamber therein for carrying a medicament containing capsule, the capsule tray being moveable through said open end between a first position at which said capsule tray is sufficiently outside said inhaler body to enable a capsule to be loaded into and unloaded from the capsule chamber and a second position inside the inhaler body beyond the point at which the first and second cutting elements are fixed and at which the capsule chamber is aligned with the inhalation passage in the upper wall and the inhalation tube in the lower wall of the body to enable inhalation of the medicament contained in the capsule through the inhalation passage.

2. A dry powder inhaler according to claim 1, wherein each of the cutting elements and its respective wall of the inhaler body are part of a single body and are made of the same material.

3. A dry powder inhaler according to claim 2, wherein the single body is a unitary moulded body.

4. A dry powder inhaler according to claim 1 wherein the inhaler body is a single unitary moulded body.

5. A dry powder inhaler according to claim 1, wherein each cutting element comprises a blade.

6. A dry powder inhaler according to claim 1, wherein each cutting element has first and second cutting parts disposed in different directions, said first cutting parts disposed to engage the capsule as the capsule tray is moved from its first position to its second position and said second cutting part disposed to engage the capsule as the capsule tray is moved from its second position to its first position.

7. A dry powder inhaler according to claim 6, wherein the cutting elements are blades and each cutting parts is a cutting edges of the blade.

8. A dry powder inhaler according to claim 6, wherein each blade has a lozenge shaped cross-section.

9. A dry powder inhaler according to claim 6, wherein each blade has a double curved cross-section.

10. A dry powder inhaler claim 6, wherein each blade is symmetrical about any axis crossing the centre of its section.

11. A dry powder inhaler according to claim 6, wherein each cutting element is configured with its cutting parts extending substantially perpendicularly from the wall of the body with which it is associated towards the other wall of the body.

12. A dry powder inhaler according to claim 11, wherein each cutting element extends from its wall for a distance such that only an extremity of a capsule is cut by said element.

13. A dry powder inhaler according to claim 12, wherein the distance that the cutting element extends from the bottom wall is less than the distance that the cutting element extends from the top wall.

14. A dry powder inhaler according to claim 1, wherein the capsule tray has opposing upper and lower walls disposed to adjoin with the upper and lower walls of the inhaler body, respectively, during insertion and removal of the capsule tray from the inhaler body opening, and the adjoining surface of at least one of said opposing upper and lower walls and upper and lower walls of the inhaler body has a textured surface adapted to reduce the build up of powder on the walls of the inhaler body opening.

15. A dry powder inhaler according to claim 14, wherein the textured surface is on the adjoining surface of both walls of the capsule tray.

16. A dry powder inhaler according to claim 14, wherein each textured surface comprises a pattern of ridges, channels or hemi-spherical projections.

17. A dry powder inhaler according to claim 14, wherein each textured surface comprises a chevron shaped pattern.

18. A dry powder inhaler according to claim 14, wherein each textured surface comprises a plurality of parallel ridges which are perpendicular to the edges of the capsule tray.

19. A dry powder inhaler according to claim 14, wherein each textured surface comprises a plurality of parallel ridges which are obliquely inclined to the edges of the capsule tray.

20. A dry powder inhaler according to claim 1, further comprising a dust cover.

* * * * *